United States Patent [19]

Hyman et al.

[11] Patent Number: 4,479,968

[45] Date of Patent: Oct. 30, 1984

[54] CONTROL OF ECTOPARASITIC INFESTATIONS OF PIGS

[75] Inventors: William B. Hyman, Kempton Park; John Hoy, Johannesburg; Philippus J. van Rensburg, Randburg, all of South Africa

[73] Assignee: The Wellcome Foundation Ltd., London, England

[21] Appl. No.: 306,327

[22] Filed: Sep. 28, 1981

[30] Foreign Application Priority Data

Oct. 17, 1980 [ZA] South Africa .................. 80/6408

[51] Int. Cl.³ .......................................... A61K 31/135
[52] U.S. Cl. ................................... 424/330; 424/190; 424/200; 424/203; 424/212; 424/213; 424/214; 424/222; 424/223; 424/278; 424/352
[58] Field of Search ............... 424/330, 212, 214, 222, 424/223, 352, 278, 200, 203, 213, 190

[56] References Cited

U.S. PATENT DOCUMENTS

| 3,544,679 | 12/1970 | McCoy | 424/358 |
| 4,070,476 | 1/1978 | Brooker et al. | 424/270 |
| 4,096,262 | 6/1978 | Andrews et al. | |
| 4,100,297 | 7/1978 | Grandadam | 424/304 |

FOREIGN PATENT DOCUMENTS 1488906 10/1977 United Kingdom.
1562908 3/1980 United Kingdom.

OTHER PUBLICATIONS

Proc. IPVS 1980 Congress, (Harrison et al.), pp. 280 & 281.
Johansson et al., Nord. Vet. Med., (1980), vol. 32, pp. 161-164.
Harrison, 1st. Pan-Hellenic Vet. Cong., (1978), pp. 1 & 6.

Primary Examiner—Sam Rosen
Attorney, Agent, or Firm—Donald Brown

[57] ABSTRACT

The invention concerns a method for the control of ectoparasitic infestations of pigs. An insecticidal composition is applied to a localized area of the pig's body surface. The composition comprises a pesticide admixed with an aliphatic hydrocarbon oil.

7 Claims, No Drawings

CONTROL OF ECTOPARASITIC INFESTATIONS OF PIGS

This invention relates to the use of insecticidal compositions on pigs.

Treatment of the pigs for ectoparasitic infestation has hitherto generally been by whole-body spraying or dipping using pesticidal formulations. These methods result in considerable wastage of the pesticide, since there is extensive run-off of the formulations from the animals. Furthermore, it has generally been believed that complete coverage of the animal's body surface with the formulation was necessary to achieve control of the infestation (see e.g. I. R. Harrison, 'The Control of Animal Ectoparasites with Particular Reference to the Use of Amitraz', 1st Pan-Hellenic Veterinary Conference (1978) at page 6).

It has now been surprisingly discovered that ectoparasitic infestations of pigs can be controlled by the use of oil-based formulations applied to a localised area of the pig's body surface, the formulation being substantially non-systemic in action.

Accordingly, this invention provides a method for the control of ectoparasitic infestations of pigs comprising the application to a localised area of the pig's body surface of a pesticidal composition comprising a pesticide admixed with an aliphatic hydrocarbon oil.

Since the composition is oily, run-off is reduced, resulting in less wastage of the pesticide. Furthermore, as pigs are difficult to handle, the method of the present invention is more convenient and easier to apply than the prior dipping and spraying methods. Using the method of the invention, no signs of toxicity such as those reported in calves in British Pat. No. 1,488,906, were observed.

The method of the invention is particularly suitable for treating infestations of lice or mange in pigs.

The pesticide in the composition used in the invention is preferably present in an amount from 0.01 to 5.0%, more preferably from 0.25 to 1.0%, by weight. Preferably, the pesticide is a non-systemic pesticide, i.e. one where penetration of the skin of the animal into the tissues and bloodstream is not required for the pesticide to be effective. This avoids contamination of the tissues of animals intended for consumption. The compositions used in the present invention do not usually contain aromatic compounds, emulsifiers or the like compounds which are known to penetrate the skin and aid penetration of the skin by other compounds.

Suitable pesticides for use in the invention include organochlorine compounds, such as lindane and dieldrin, organophosphates such as diazinon, coumaphos and malathion, pyrethroids such as permethrin, cypermethrin, deltamethrin, fenvalerate, cyhalothrin, plumethrin and BAYTHROID (Trade Mark) and formamidines such as amitraz. Amitraz is a particularly preferred pesticide and is N-methyl-bis(2,4-dixylyliminomethyl) amine.

Compositions used in the invention may, in addition, include a pigment or a dye. The advantage of having a pigment or dye present is that it is easy to see which animals in a batch have been treated and how effective the composition is in being retained on the skin of the animal.

The aliphatic hydrocarbon oil may be any suitable liquid aliphatic hydrocarbon, e.g. liquid paraffin or another paraffinic oil. ESSO base oil 45581 which is a relatively narrow cut predominantly paraffinic highly refined straight petroleum oil is a very convenient oil to use. The concentration of the insecticide in the oil can vary, depending on the activity of the insecticide. Thus, as mentioned above, concentrations of from 0.01-5% by weight are suitable and a general range of concentration for amitraz, lindane, diazinon or a pyrethroid insecticide may be in the range of 0.1-2.5%.

Such compositions are simple to make and use. Thus, they can be made by any suitable mixing (e.g. dissolving, micronising and dispersing, etc.) techniques. The composition can be applied by simple pouring on to the animal and its diseased parts, e.g. with a bucket and spoon or, if convenient, with more sophisticated applicators.

The invention will now be described, by way of example, with reference to the following non-limiting Examples. Deltamethrin is (S)-alpha-cyano-3 phenoxybenzyl (+) cis-3(2,2-dibromovinyl)-2,2 dimethylcyclopropane-1-carboxylate.

EXAMPLE 1

Compositions as defined in Table 1 were made by admixing the components together.

In the case of the lindane, diazinon and amitraz, the various ingredients were simply dissolved in ESSO base oil 45581. In the case of the amitraz, propylene oxide was added as a chemical stabilizer to prevent degradation in storage.

The three compositions containing deltamethrin are not in accordance with the invention as they are systemic compositions. In deltamethrin I, the aromatic solvent was added to the base oil to ensure that the deltamethrin dissolved in the solution, and the same applied to the deltamethrin II. The aromatic solvent (xylene) is known to penetrate the skin.

In the case of deltamethrin III, the deltamethrin was in solid form and very finely milled to form a colloidal suspension in water. The water containing the colloidal deltamethrin was then formed into an emulsion with the aliphatic base oil, using SPAN 85 as an emulsifier, and the balance of the composition, not shown in Table I, amounted to water.

Fat orange is an oil-soluble dye available from Hoechst AG as R-type 8073; the aromatic solvent is that available from Esso Chemicals (Proprietary) Limited as Solvesso 200.

The efficacy of the compositions was tested on light infestations of *sarcoptes scabiei* (pig mange) and found to be effective.

EXAMPLE 2

The compositions of Table 2 were then tested on extremely heavy infestations of pig mange in an 80 sow pig herd.

The entire herd had been dipped three times previously in a dipping tank. Dipping was initially carried out with lindane (i.e. the organo chlorine compound known as gamma-benzene hexachloride or hexachlorocyclohexane) powder made up to a dipping fluid according to the manufacturer's instructions. Ten days later the process was repeated, using a diazinon and rotenone dip wash made up according to the distributor's instructions. (Diazinon is an organo phosphate known as O,O-diethyl O-2-isopropyl-6-methylpyrimidin-4-yl phosphorothioate and rotenone is derris root extract). The dipping with diazinon and rotenone was repeated 10 days later, but no improvement was observed. It was at this stage that the compositions according to Table 1 were tested.

Six groups of the most severely affected weaners, approximately ten weeks old, were selected. All groups were housed on concrete pens with both roofed and open runs, fed on a commercial grower ration, watered by nipple, and were approximately of the same weight. All groups consisted of piglets selected according to size at weaning.

The seven formulations of Table 1, including the control comprising only the base aliphatic oil, were used.

After an initial examination to determine the degree of infestation (which was found to be extremely high) from skin scrapings taken from the face, lateral neck, back and tail root, together with detritus removed from the ear canals, examined in liquid paraffin under a microscope, the pigs were individually treated at a rate of 5 mg/kg by applying the formulations by means of a plastic disposable syringe in a stripe down the backline and across the head behind the ears.

Seven days later the procedure was repeated, after the same examination of the scrapings. However, in the case of the control group there had been deterioration including the death of a piglet, so that treatment with deltamethrin at a dosage of about about 2.5 mg/kg was carried out.

Seven days later, scrapings were examined as before, but only the control group was treated, again at a dosage rate of 2.5 mg/kg, using a dosing gun having a spray gun nozzle head.

A week later, further scrapings were taken, together with scrapings from a comparative sample of untreated pigs, and about two weeks later a further set of scrapings was collected and submitted to an independent authority for examination.

During the treatment, apart from normal cleaning and hosing, no treatment was applied to the pigs in any of the pens during the duration of the trial.

The details of the trial are set out in Table II.

TABLE 1

| Type of Pour-on | Active Ingredient Concentration (Technical) | | Fat Orange | | Base Oil | | Propylene Oxide | | Aromatic Solvent | Emulsifier |
|---|---|---|---|---|---|---|---|---|---|---|
| | g/100 ml | g/100 g | g/100 ml | g/100 g | g/100 ml | g/100 g | g/100 ml | g/100 g | g/100 ml | g/100 ml |
| Lindane | 1.00 | 1.18 | 0.05 | 0.06 | 83.75 | 98.76 | — | — | — | — |
| Diazinon | 1.05 | 1.24 | 0.05 | 0.06 | 82.90 | 98.11 | — | — | — | — |
| Amitraz | 1.00 | 1.18 | 0.05 | 0.06 | 83.15 | 98.52 | 0.2 | 0.24 | — | — |
| Deltamethrin I (for control) | 0.25 | — | 0.05 | — | To volume | | — | — | 15.0 | — |
| Deltamethrin II (for control) | 0.5 | — | 0.05 | — | To volume | | — | — | 15.0 | — |
| Deltamethrin Control | 0.5 | — | — | — | 66.5 Straight Base Oil | — | — | — | — | 3.5 |

TABLE II

BIOLOGICAL DATA

| No. of Animals treated (in each pen) | 19 | | | 20 | | | 21 | | | 21 | | | 21 Control | | | 21 | | |
|---|---|---|---|---|---|---|---|---|---|---|---|---|---|---|---|---|---|---|
| Formulation Used | Lindane | | | Diazinon | | | Amitraz | | | Deltamethrin II (0,5%) | | | NIL | Deltameth-rin I * * | | Deltamethrin III | | |
| Examination No. | 1st | 2nd | 3rd | 1st | 2nd | 3rd | 1st | 2nd | 3rd | 1st | 2nd | 3rd | 1st | 2nd | 3rd | 1st | 2nd | 3rd |
| Eggs | X | x | x | x | x | X | x | X | X | X | X | X | x | X | X | x | X | X |
| Larvae | +4 | +3 | + | +4 | +2 | O | +4 | — | — | +4 | — | — | +4 | +4 | O | +4 | — | — |
| Nymphs | +4 | +3 | + | +4 | +2 | O | +4 | — | — | +4 | — | — | +4 | +4 | O | +4 | — | — |
| Adults | +4 | +3 | + | +4 | — | O | +4 | — | — | +4 | — | — | +4 | +4 | O | +4 | — | O |

LEGEND
+4 = 20–40 live per field
+3 = 10–20 live per field
+2 = 1–10 live per field
+ = 1 live per field
— = 0 live per field.
X = No eggs seen
x = Eggs present
O = Dead parasites present
* = Treated with Deltamethrin I The first treatment with amitraz, deltamethrin II, and deltamethrin III eliminated all stages of the parasite, and the two treatments with deltamethrin I eliminated live parasites from the control group.

After one treatment with diazinon, the infestation was reduced and only dead carcasses could be found after the second treatment.

The lindane in turn was found to reduce the infestation to a light level after two treatments.

Scrapings taken 21 days after the first treatment and 14 days after the second treatment (except for the control group), revealed no parasites in any of the treated groups. All the trial groups, including the controls, were free from pruritis and scurfiness. The control, lindane and diazinon groups, however, had not shown the same growth as the amitraz and deltamethrin II groups, which were at this stage bigger, sturdier, and had smoother skins.

Twenty three days after the last treatment, the control group was again examined. Their growth was stunted compared with the others, and a slight pruritis was present in the group.

The second application of deltamethrin I appeared to have removed the parasites from the control group but it appears that live parasites or viable eggs must have remained to ensure continuance of the infestation.

No penetration of the skin occurred with the compositions of the invention. From the above it is seen that the invention provides a number of effective formulations for the treatment of pig mange and which have the advantages of acting in a nonsystemic manner.

EXAMPLE 3

Two compositions were made by dissolving amitraz in Esso base oil 45581. The concentrations by weight of the amitraz were 0.5% and 1.0% respectively.

Six groups of *sarcoptes scabiei* infected 3-month old pigs were treated with one of the compositions by applying the composition with a syringe down the centre of the topline from forehead to tail base. There were intervals of 9 days between the first and second treatments and 8 days between the second and third treatments.

The treatment system was as follows

| 0,5% amitraz pour-on | | | | 1,0% amitraz pour-on | | | |
|---|---|---|---|---|---|---|---|
| Group | No. Pigs | Dose mg/kg | No. Treatments | Group | No. Pigs | Dose mg/kg | No. Treatments |
| 4 | 4 | 5 | 1 | 1 | 4 | 5 | 1 |
| 5 | 5 | 5 | 2 | 2 | 4 | 5 | 2 |
| 6 | 3 | 2,5 | 2 | 3 | 4 | 5 | 3 |

No live mites were found in scrapings taken at the final examination. A single treatment took longer to clear the infestations than two treatments. Similarly two treatments took longer to clear the infestations than three treatments.

The acute dermal $LD_{50}$ and the acute oral $LD_{50}$ of the 1% mixture in female Sprague-Dawley rats were greater than 10 ml/kg.

However, although the invention has been described above with reference to the treatment of pigs having pig mange, it is to be explicitly understood that the invention is not limited to the treatment of pig mange.

Apart from this advantage, it must be emphasized that the Applicant's residue and toxicity trials have confirmed that there is no systemic effect, and the invention permits the use of a low active ingredient content (such as 0.01-5%, typically 0.25 to 1%) with high carrier volumes. Furthermore, the invention allows carriers to be used having no solvents or emulsifiers and viscosities of up to 12.9 centistokes at 40° C.

We claim:

1. A method for control of ectoparasitic infestations of pigs, consisting essentially of the topical application to a localized area of the pig's body surface of a pesticidal composition consisting essentially of an aliphatic hydrocarbon oil as the only organic hydrocarbon oil and a nonsystemic acting pesticidal compound selected from the class consisting of organochlorine, organophosphate, pyrethroid and formamidine compounds.

2. A method as claimed in claim 1, in which the ectroparasitic infestation is of lice or mange.

3. A method as claimed in claim 1, in which the pesticide is present in the pesticidal composition in an amount of 0.01 to 5.0% by weight.

4. The method of claim 1 in which the composition is applied as a stripe down the backline and across the head behind the ears of the pig.

5. The method of claim 4 in which the pesticide is Amitraz.

6. A method as claimed in claim 1 in which the ectoparasitic infestation is manage.

7. The method of claim 6 in which the pesticide is Amitraz.

* * * * *